United States Patent [19]

Iwakoshi et al.

[11] Patent Number: 4,836,187
[45] Date of Patent: Jun. 6, 1989

[54] CONSTANT PRESSURE APPARATUS OF AN ENDOSCOPE

[75] Inventors: Keiichi Iwakoshi, Nasu; Mitsuru Sato, Shibuya; Hiroyuki Umeda, Kasukabe; Toshinori Nishizawa, Mitaka, all of Japan

[73] Assignees: Kabushiki Kaisha Toshiba, Kawasaki; Kabushiki Kaisha Machidaseisakujyo, Tokyo, both of Japan

[21] Appl. No.: 137,943

[22] Filed: Dec. 28, 1987

[30] Foreign Application Priority Data

Dec. 27, 1986 [JP] Japan .................................. 61-311892

[51] Int. Cl.$^4$ .............................................. A61B 1/00
[52] U.S. Cl. ....................................................... 128/4
[58] Field of Search ........................................ 128/4, 6

[56] References Cited

U.S. PATENT DOCUMENTS 4,349,014 9/1982 Takamatsu .............................. 128/6

Primary Examiner—William H. Grieb
Attorney, Agent, or Firm—Foley & Lardner Schwartz, Jeffery, Schwaab, Mack, Blumenthal & Evans

[57] ABSTRACT

A constant pressure apparatus of an endoscope includes a gas supplying conduit for cleaning an optical observation system, a sucking conduit for constantly holding the inner pressure of a body, and an insertion port for inserting a device for medical treatment into the body. The constant pressure apparatus comprises a pressure detector disposed in a portion of the gas supplying conduit and detecting the pressure in the gas supplying conduit. The pressure detector is electrically connected to a control device for controlling the inner pressure of the body. A gas supplying device for adjusting the inner pressure of the body is disposed in the insertion port and may comprise a fiber for transmitting laser into which a cooling conduit for receiving carbon dioxide is inserted. Electromagnetic valves are disposed in the gas supplying conduit, the sucking conduit and the gas supplying means, respectively, and are operated by signals from the control device.

13 Claims, 2 Drawing Sheets

CONSTANT PRESSURE APPARATUS OF AN ENDOSCOPE

The present invention relates to an improvement of a constant pressure endoscope for medical care, and in particular, to an improvement of a constant pressure endoscope which can easily adjust the inner pressure of a human body without using any special means for detecting the inner pressure of the Human body during operation of the apparatus.

BACKGROUND OF THE INVENTION

An endoscope is widely used to examine and cure portions of a human's body such as duodenum, rectum, large intestine, esophagus, ears, nose, and bladder.

In the examination and medical care of the human body by an endoscope, it is sometimes necessary to constantly adjust the inner pressure of the Human body. Namely, when a diseased stomach, etc., are treated, it is necessary to see changes in the sizes of diseased portions of ulcer, etc., in medical processes under the same pressure condition, so that it is required to adjust the inner pressure of the human body in every medical care.

When medical care is performed by an endoscope provided with a laser knife, carbon dioxide gas is discharged from an end of a laser incineration probe to protect an optical fiber for guiding the laser. In this case, it is necessary to hold the inner pressure of the Human body constant to guarantee that the carbon dioxide gas is not sucked into a diseased portion of a patient and the diseased portion is thereby expanded.

A constant pressure apparatus for an endoscope is used in accordance with the requirement mentioned above. The conventional constant pressure apparatus is constituted by means for supplying a gas into a human's body, means for sucking the gas from the human's body, and a detector for detecting the inner pressure within the human'body.

In the conventional constant pressure apparatus of the endoscope mentioned above, it is necessary to insert the inner pressure detector into a channel therefor. Therefore, a normally general endoscope cannot be used in examination and medical care required to adjust the inner pressure of the human's body.

Namely, conventionally, an endoscope body and the inner pressure detector are incorporated to perform examination and medical care. Accordingly, as shown in FIG. 1, only a dedicated endoscope provided at an end thereof 200 with a channel 100 for the inner pressure detector of the human's body can be used in the examination and medical care required to adjust the inner pressure of the human's body.

SUMMARY OF THE INVENTION

To solve the problems mentioned above, an object of the present invention is to provide a constant pressure apparatus for an endoscope which can easily adjust the inner pressure of a human's body without using any special means for detecting the inner pressure of the human's body.

With the above object in view, the present invention resides in a constant pressure apparatus of an endoscope comprising a conduit for supplying gas to clean an optical observation system, a sucking conduit for constantly holding the inner pressure of a human's body portion, and an insertion port for inserting a device required to cure the human's body. The constant pressure apparatus further comprises means detecting the pressure in the gas supplying conduit in a portion thereof and electrically connected to a control device for controlling the inner pressure of the human's body.

In the constant pressure apparatus of the endoscope in the present invention, the pressure detecting means is disposed in the gas supplying conduit used to clean the optical observation system at an end of the endoscope. Therefore, the gas supplying conduit also functions as a channel for detecting the inner pressure within the human's body so that the inner pressure of the human's body can be easily adjusted without using any special apparatus and means.

Accordingly, in the constant pressure apparatus of the endoscope in the present invention, it is possible to perform examination and medical care required to adjust the inner pressure of the human's body by using a normal endoscope, thereby further improving function and generalization of the endoscope.

BRIEF DESCRIPTION OF THE DRAWINGS

The present invention will be more apparent from the following preferred embodiments thereof in conjunction with the accompanying drawings in which.

DETAILED DESCRIPTION OF THE PREFERRED EMBODIMENTS

The preferred embodiments of a constant pressure apparatus of an endoscope in the present invention will now be described in detail with reference to the drawings.

Figure 1:
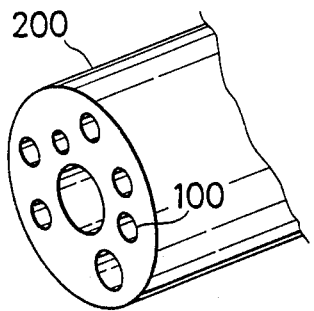
FIG. 1 is a partially enlarged perspective view showing an end portion of a conventional endoscope provided with a channel for a detector for detecting the inner pressure within a human's body.
Figure 2:
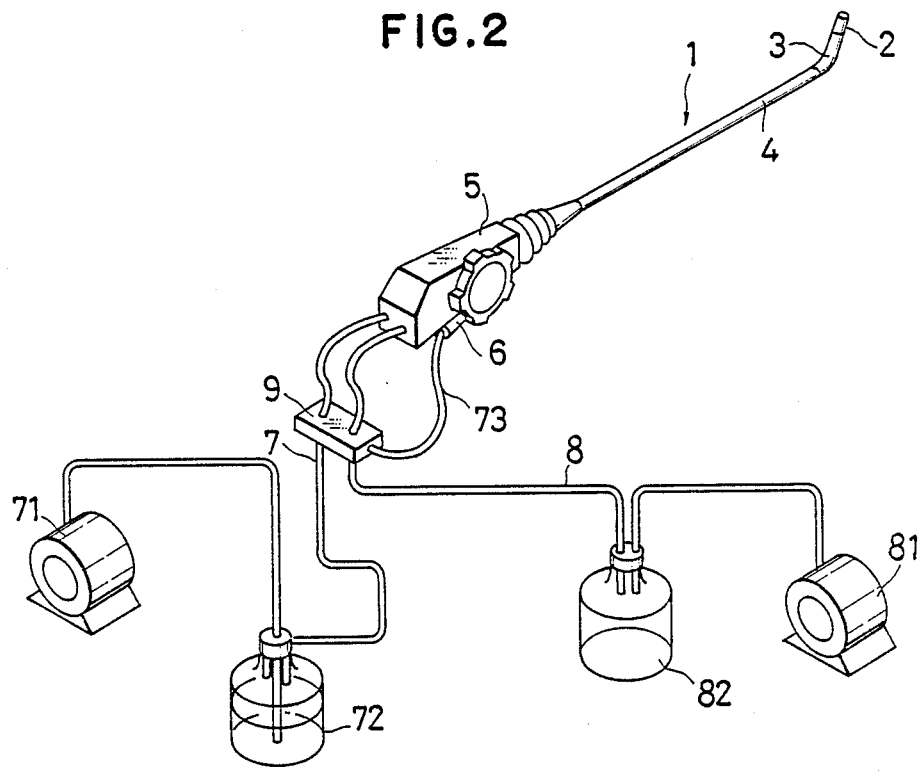
FIG. 2 is a perspective view schematically showing a constant pressure apparatus of an endoscope in accordance with the present invention.

In FIG. 2, an endoscope 1 in the present invention includes an end portion 2 for disposing therein a solid image pick up element (called a CCD in the following description), an optical observation system, etc., a bent portion 3 moved by the operation of an operator upward, downward, right and left, a guide portion 4 connected to the bent portion 3, and an operating portion 5 connected to the guide portion 4.

The operating portion 5 has an insertion port 6 for inserting a device for medical care used to check a human's body, etc., an operating knob for actuating the bent portion 3, various kinds of operating buttons which are not shown, and a power source section. The operating portion 5 is connected to a gas supplying conduit 7 and a sucking conduit 8.

Figure 3:
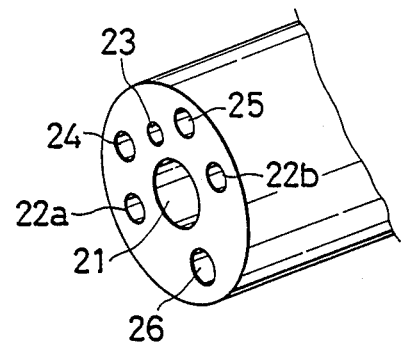
FIG. 3 is a partially enlarged perspective view showing an end portion of the endoscope of FIG. 2.
Figure 4:
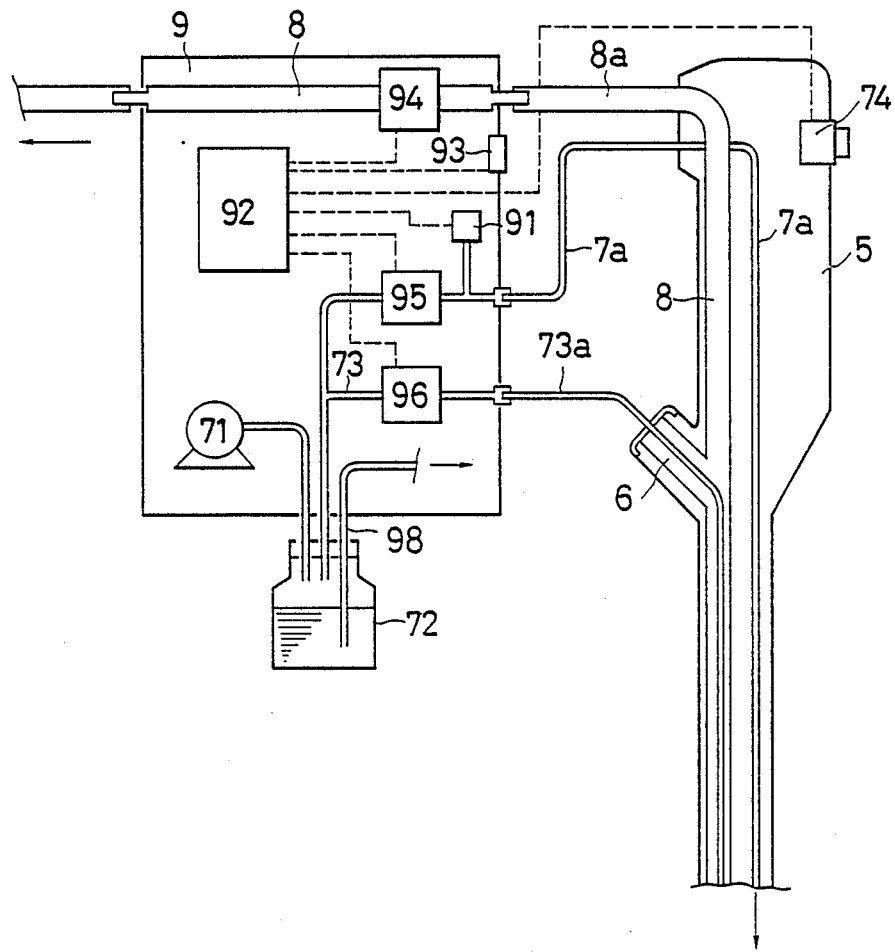
FIG. 4 is a view for the connection relation between conduits and circuits in accordance with one embodiment of the constant pressure apparatus of the endoscope in the present invention.

One end of the gas supplying conduit 7 is connected to a liquid supplying bottle 72 connected to a gas supplying pump 71, and one end of the sucking conduit 8 is connected to a sucking bottle 82 connected to a sucking pump 81. The other ends of the gas supplying conduit 7 and the sucking conduit 8 are respectively connected to a gas supplying nozzle 23 and a sucking nozzle 24 dosposed at an end of the endoscope shown FIG. 3.

a liquid supplying conduit is omitted in FIGS. 2 and 4, but is normally connected, similar to the gas supplying conduit 7, from the liquid supplying bottle 72 to a liquid supplying nozzle 25 at the end of the endoscope as shown in FIG. 3.

In FIG. 3, the end of the endoscope has an optical observation system 21 constituted by a lens window for storing a CCD, etc., therein, fibers 22a and 22b for illumination, the gas supplying nozzle 23, the sucking nozzle 24, the liquid supplying nozzle 25, and an outlet port 26 used to check a human's body, etc. The gas supplying nozzle 23 and the liquid supplying nozzle 25 are used to remove fouling, etc., attached onto surfaces of the optical observation system 21 during the operation of the apparatus and clean them.

In the constant pressure apparatus of the endoscope in the present invention constituted above, a pressure detector is disposed in a portion of the gas supplying conduit 7, and detects the pressure in the gas supplying conduit 7, and is electrically connected to a control device for controlling the inner pressure of a human's body so as to automatically adjust the gas supplying and sucking operations.

Namely, as shown in FIG. 4, a controller 9 in the constant pressure apparatus of the endoscope in the present invention is constituted by the pressure detector 91 such as a semiconductor transducer mainly branched from a portion of the gas supplying conduit 7 where the pressure detector may be the same one as the one used in the conventional constant pressure apparatus, the control device 92 for controlling the inner pressure of a human's body, an electromagnetic valve 94 dosposed in the sucking conduit 8, an electromagnetic valve 95 disposed in the gas supplying conduit 7, and an electromagnetic valve 96 disposed in a branched gas supplying conduit 73.

A gas supplying conduit 7a extending ahead from the pressure detector 91 to the end of the endoscope is open toward the human's body so that the gas supplying conduit 7a has the same pressure as the one within the human's body at any time in a state in which the electromagnetic valve 95 is closed. Accordingly, an exact inner pressure of the human's body can be instructed by the pressure detector 91 to the control device 92 for controlling the inner pressure of the human's body.

When th eelectromagnetic valve 95 is open, the gas is supplied into the gas supplying conduit 7 so that the pressure detector 91 cannot detect the inner pressure of the human's body. However, since the time for supplying the gas to clean the end portion 2 of the endoscope is short, the control device 92 may hold an indicated value of the pressure detector 91 immediately before the electromagnetic valve 95 is open, for example, thereby causing no problems.

The gas supplying conduit 7 is branched to the branched gas supplying conduit 73 as another gas supplying means, and the branched gas supplying conduit 73 is inserted into the endoscope from the insertion port 6 to supply the gas to the outlet port 26 at the end of the endoscope. Accordingly, the gas supplying conduit 7a may be used to clean the end portion of the endoscope, and the branched gas supplying conduit 73 may be used to hold the inner pressure of the human's body so that the number of opening and closed operations of the electromagnetic valve 95 is reduced, thereby improivving the detecting ability of the pressure detector 91.

The branched gas supplying conduit 73 may be omitted in a certain condition in which three functions comprising the detection of the inner pressure within the human's body, the cleaning of the end poriton of the endoscope, and the holding of the inner pressure can be performed by only the gas supplying conduit 7.

The fluid in the sucking conduit 8 is sucked by the sucking pump 81 (FIG. 2) at any time during the operation of the apparatus, but the electromagnetic valve 94 is normally closed so that a sucking conduit 8a extending ahead from the electromagnetic valve 94 is in a rest state of sucking.

The gas is supplied by the gas supplying pump 71 through the gas supplying conduit 7 and the branched gas supplying conduit 73 at any time during the operation of the apparatus, but the electromagnetic valves 95 and 96 are normally closed so that gas supplying conduits 7a and 73a extending ahead from the electromagnetic valves 95 and 96 are in a rest state of sucking.

When the optical observation system 21 at the end of the endoscope 1 is cleaned, an operator pushes a gas supplying switch 74 and a liquid supplying switch (not shown) to turn them on so that the electromagnetic valve 95 is opened and the gas is supplied to the gas supplying conduit 7a, thereby cleaning the optical observation system 21.

The control device 92 for controlling the inner pressure of a human's body instructs the opening and closing of the electromagnetic valves 94, 95 and 96 based on the results obtained by comparing a pressure value indicated by the pressure detector 91 with a pressure value set in an operating panel 93 in advance.

Accordingly, when the pressure detector 91 detects that the inner pressure of the human's body is higher than the set pressure value during the operation of the apparatus, the ocntrol device 92 instructs the opening of the electromagnetic valve 94 so that the sucking operation in the sucking conduit 8 is performed. When the inner pressure of the human's body is lower than the set pressure value, the control device 92 instructs the closing of the electromagnetic valve 94.

When the pressure detector 91 detects that the inner pressure of the human's body is lower than the set pressure value, the control device 92 instructs the opening of the electromagnetic valve 96 so that the gas is supplied to the branched gas supplying conduit 73. When the pressure detector 91 detects that the inner pressure of the human's body is higher than the set pressure value, the control device 92 instructs the closing of the electromagnetic valve 96.

In the operation of the apparatus mentioned above, the inner pressure of the human's body by supplying the gas can be held by opening both the electromagnetic valves 95 and 96.

As mentioned above, in the constant pressure apparatus of the endoscope of the present invention, the pressure detector 91 is disposed in the gas supplying conduit 7 and a pressure value detected by the pressure detector 91 is transmitted to the control device 92 for controlling the inner pressure of the human's body to instruct the opening of the electromagnetic valves 94, 95 and 96, thereby automtically adjusting hte inner pressure of the human's body without using any special apparatus and means.

Further, in medical care using a laser knife, a fiber transmitting laser and provided with a conduit for carbon dioxide may be inserted into the insertion port 6 instead of the branched gas supplying conduit 73. In this case, the pressure of the supplied gas except for the pressure by the carbon dioxide may be compensated by the gas supplying conduit 7 and the electromagnetic valve 95.

Further, in FIG. 4, the prevent invention can be applied even when the electromagnetic valve 94 and a liquid supplying conduit 98 of the liquid supplying bottle 72 are separately disposed.

As mentioned above, in a constant pressure apparatus of an endoscope in the present invention, a pressure detector is disposed in a gas supplying conduit used to clean an optical observation system disposed at an end of the endoscope and detects the pressure in the gas supplying conduit, and the gas supplying conduit also functions as a channel for detecting the inner pressure of a human's body, so that the inner pressure of the human's body can be easily adjusted without using any special apparatus and means.

Accordingly, in the constant pressure apparatus of the endoscope in the present invention, it is possible to perform examination and medical care required to adjust the inner pressure of the human's body using a normal endoscope, thereby further improving function and generalization of the endoscope.

The present invention is not limited to the embodiments of the electronic endoscope of the present inveniton mentioned above, but a conventionally used fiber scope can be applied to the present invention as a modified embodiment.

What is claimed is:

1. A system for regulating the gas pressure within a cavity, comprising:
   a probe for insertion into the cavity;
   a suction line having one end disposed within the probe for removing gas from the cavity;
   a valve connected to the other end of the suction line;
   a first gas supply line also having one end disposed within the probe;
   a valve connected to the other end of the gas supply line;
   a pressure detecting means connected to the other end of the gas supply line between the valve and the probe;
   a second gas supply line having one end disposed within the probe;
   a valve connected to the other end of the second gas supply line; and
   a control means for receiving an indication of the pressure detected by the pressure detecting means when the first gas supply line is closed and selectively opening and closing the valves in the suction line and the second gas supply line to achieve the desired gas pressure within the cavity.

2. The system of claim 1, in which the probe is part of an endoscopic instrument.

3. The system of claim 1, in which the control means additionally regulates the opening and closing of the first gas supply line to maintain a constant pressure within the cavity.

4. The system of claim 3, in which the pressure detecting means operates only when the valve on the first gas supply line is closed.

5. The system of claim 1, in which the second gas supply line enters the probe through an insertion port.

6. The system of claim 1, in which the valve on the control means regulates the opening and closing of the valves on each of the first gas supply line, the second gas supply line and the suction line by comparing the pressure actually measured within the cavity to a predetermined pressure value.

7. The system of claim 1, in which the first gas supply line supplies gas, as needed, to the probe in order to clean the optical system thereof.

8. The system of claim 7, further including a control means for opening the valve controlling the supply of gas through the first gas supply means, in order to supply cleaning gas when the pressure detecting means is not functioning and to measure the pressure within the cavity when cleaning gas is not being supplied.

9. A constant pressure apparatus for an endoscope including an optical observation system at its end portion, an injective conduit means for transmitting a gas to clean the optical observaiton system, and an insertion port means through which a medical device may be inserted, the constant pressure apparatus comprising:
   pressure measuring means connected to a portion of hte injective conduit means outside of the scope section for measuring the pressure inside the injective conduit means;
   extractive conduit means for maintaining the inner pressure of a body to be examined; and
   means for controlling the inner pressure of the body by controlling gas transmissions through the injective conduit means and the extractive conduit means.

10. The apparatus of claim 9 further comprising sescond injective conduit means disposed in the insertion port means for maintaining the inner pressure of the body exhaling gases.

11. The apparatus of claim 10 wherein the second injective conduit means contains therein a fiber for transmitting laser beams and a conduit for supplying carbon dioxide coolant.

12. The apparatus of claim 10 further comprising electromagnetic valves disposed in the injective conduit means, extractive conduit means, and the second injective conduit means, and wherein the controlling means controls gas transmissions through the injective conduit means, the extractive conduit means, and the second injective conduit means by controlling the opening and closing of each of the electromagnetic valves.

13. The apparatus of claim 12 wherein the controlling of the electromagnetic valves by the controlling means is carried out in accordance with a comparison of the pressure measured by the pressure measuring means with respect to a predetermined pressure.

* * * * *